Figure 1:
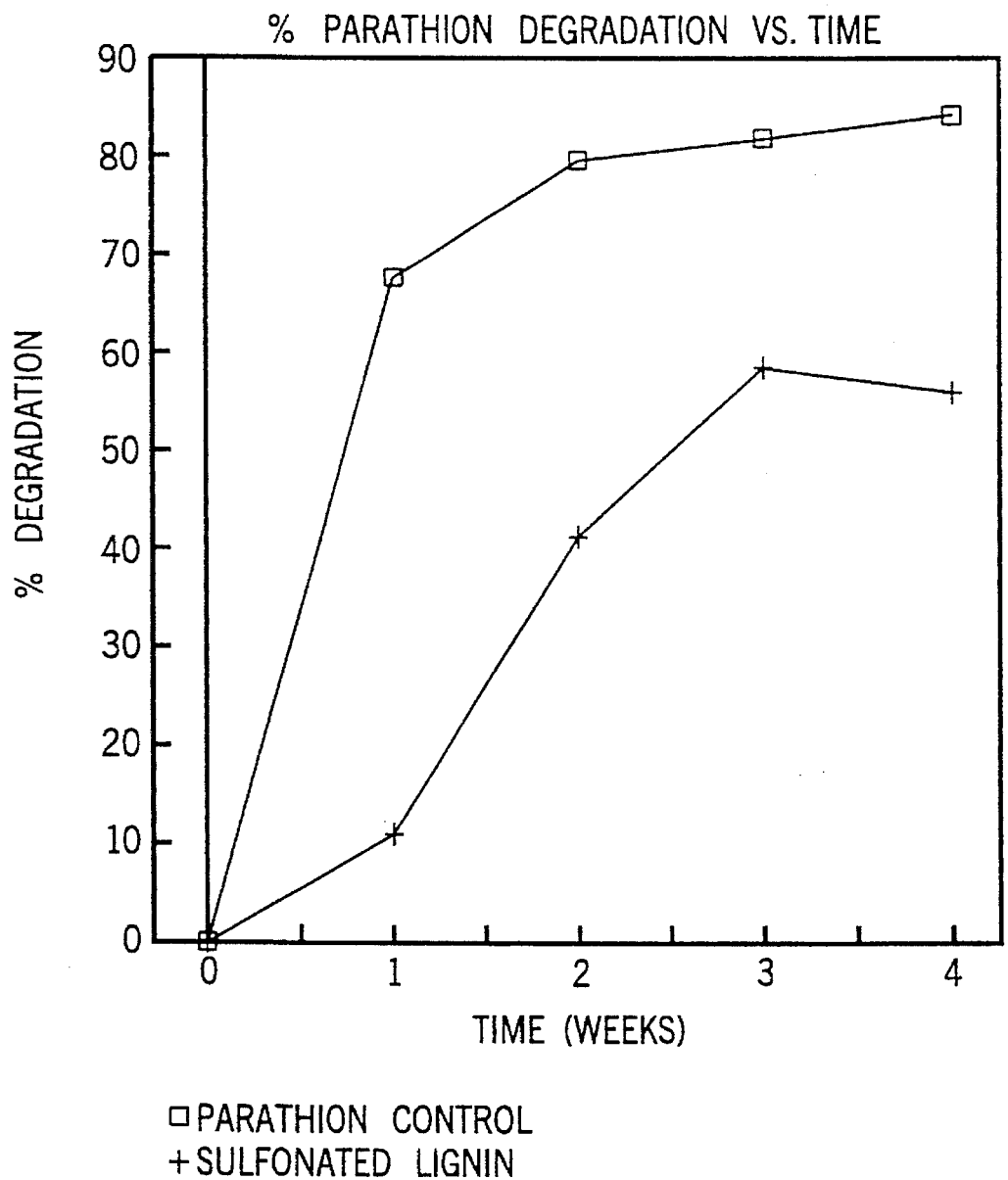
Figure 2:
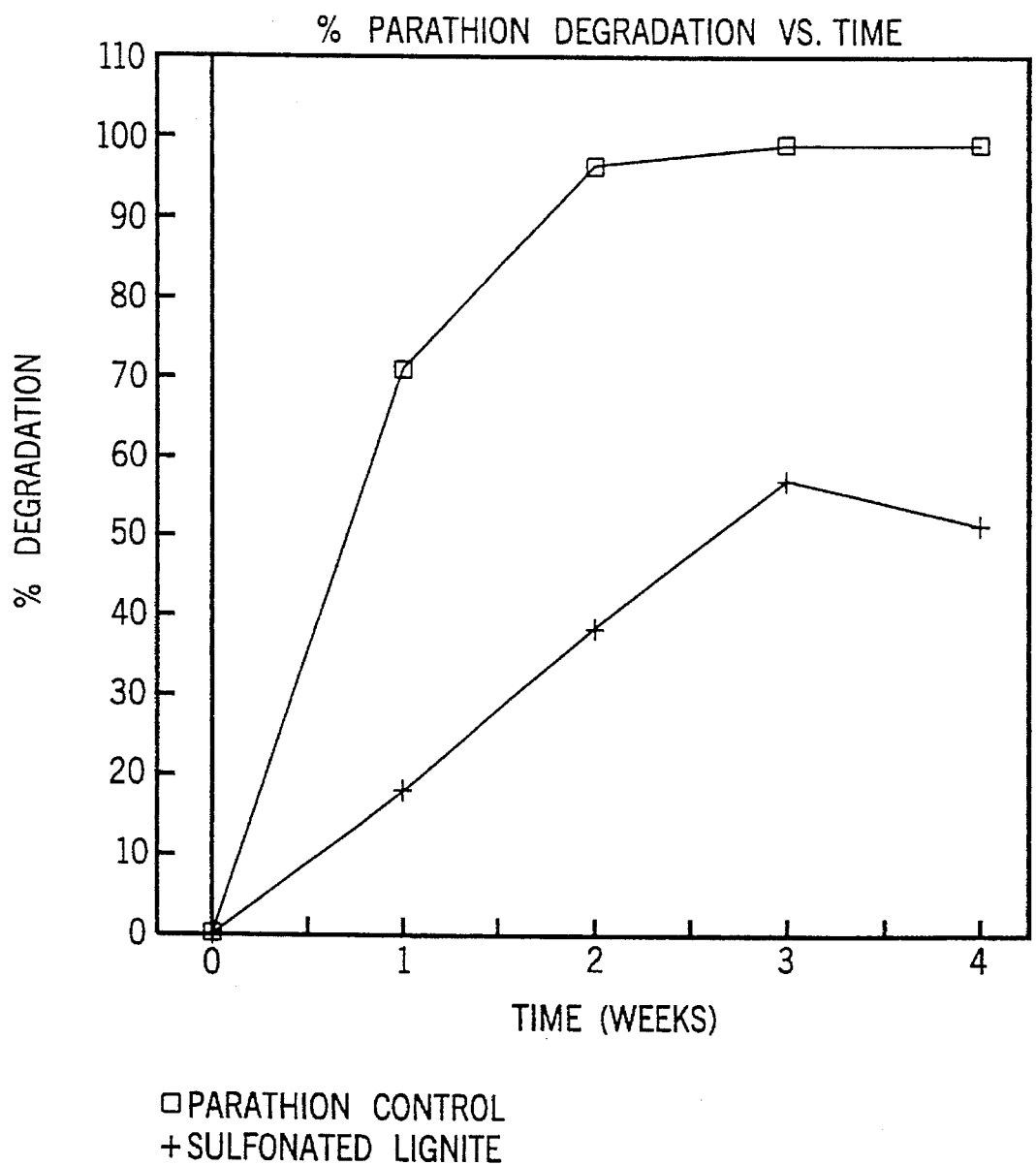
Figure 3:
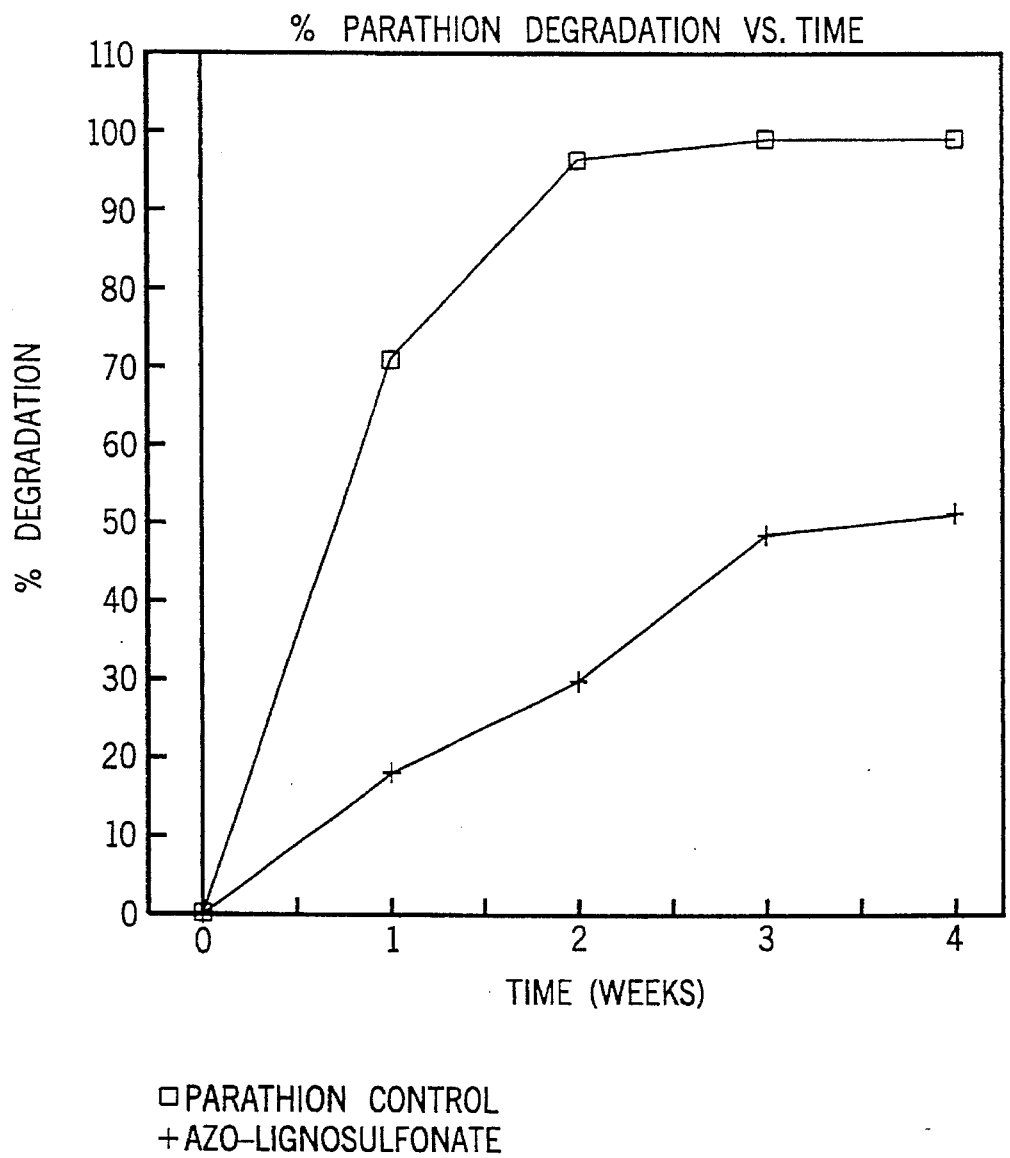
Figure 4:
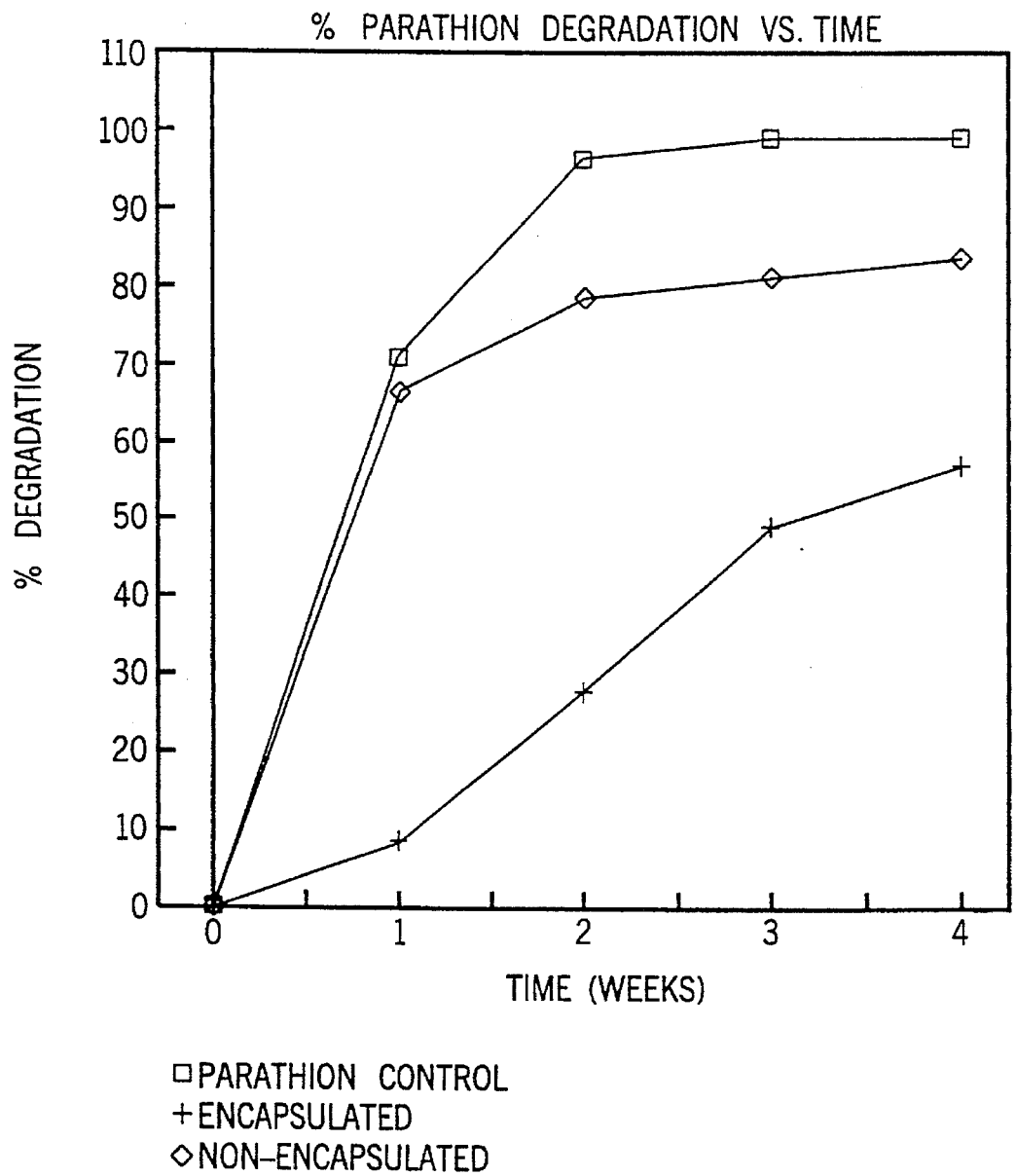

United States Patent [19]

Lebo, Jr. et al.

[11] Patent Number: 5,552,149
[45] Date of Patent: Sep. 3, 1996

[54] METHOD FOR MICROENCAPSULATION OF AGRICULTURALLY ACTIVE SUBSTANCES

[75] Inventors: Stuart E. Lebo, Jr.; William J. Detroit, both of Schofield, Wis.

[73] Assignee: Lignotech USA, Inc., Rothschild, Wis.

[21] Appl. No.: 133,896

[22] Filed: Oct. 12, 1993

[51] Int. Cl.$^6$ .................. A01N 25/34; B01J 13/10; B01J 13/20
[52] U.S. Cl. .............. 424/408; 71/DIG. 1; 252/589; 264/4.1; 264/4.3; 424/418
[58] Field of Search .................. 252/589; 264/4.1, 264/4.3, 4.7; 514/963; 424/408, 491, 418; 71/DIG. 1

[56] References Cited

U.S. PATENT DOCUMENTS

| | | | |
|---|---|---|---|
| Re. 29,238 | 5/1977 | Dimitri et al. | 71/101 |
| 2,090,109 | 8/1937 | Coe | 427/407 |
| 2,800,458 | 7/1957 | Green | 264/4.3 X |
| 3,242,051 | 3/1966 | Hiestand et al. | 264/4.3 X |
| 3,505,254 | 4/1970 | Kidwell et al. | 523/202 |
| 3,839,561 | 10/1974 | Bordenca | 424/174 |
| 4,007,258 | 2/1977 | Cohen et al. | 71/DIG. 1 |
| 4,056,610 | 11/1977 | Barber, Jr. et al. | 424/419 |
| 4,094,969 | 6/1978 | Batzer et al. | 424/78 |
| 4,184,866 | 1/1980 | DelliColli et al. | 71/65 |
| 4,223,007 | 9/1980 | Spence et al. | 424/418 |
| 4,244,728 | 1/1981 | DelliColli et al. | 71/65 |
| 4,244,729 | 1/1981 | DelliColli et al. | 71/65 |
| 4,280,833 | 6/1981 | Beestman et al. | 71/100 |
| 4,344,857 | 8/1982 | Shasha et al. | 504/244 |
| 4,402,856 | 9/1983 | Schnoring et al. | 71/DIG. 1 |
| 4,417,916 | 11/1983 | Beestman et al. | 71/93 |
| 4,497,793 | 2/1985 | Simkin | 264/4.7 X |
| 4,557,755 | 12/1985 | Takahashi et al. | 264/4.7 X |
| 4,753,799 | 6/1988 | Nelsen et al. | 424/408 |
| 4,808,408 | 2/1989 | Baker et al. | 424/408 |
| 4,844,896 | 7/1989 | Bohm et al. | 424/89 |
| 4,846,888 | 7/1989 | Detroit | 106/93 |
| 4,938,797 | 7/1990 | Hasslin et al. | 71/118 |
| 5,023,024 | 6/1991 | Kyogoku et al. | 264/4.3 |
| 5,292,533 | 3/1994 | McMahon et al. | 424/408 |

FOREIGN PATENT DOCUMENTS

| | | |
|---|---|---|
| 0025379 | 8/1979 | European Pat. Off. . |
| WO92/19102 | 2/1992 | WIPO . |

OTHER PUBLICATIONS

"What's New in the Ever–Changing World of Micro and Macroencapsulation", Suzanne Christiansen, Soap/Cosmetics/Chemical Specialties, Sep., 1992, pp. 26–28.

Primary Examiner—Richard D. Lovering
Attorney, Agent, or Firm—Andrus, Sceales, Starke & Sawall

[57] ABSTRACT

A method for microencapsulating agriculturally active substances such as pesticides to provide improved resistance to environmental degradation, especially ultra-violet light. The method employs as the UV protectant lignosulfonates, such as sulfite lignin or sulfonated lignin, or alternately sulfonated lignite, sulfonated tannins, napthalene sulfonates or other related compounds in combination with a protein such as a high bloom gelatin to form a capsule wall. The capsule wall formed by the interaction of these components is durable and has an ultra-violet protectant as an integral part of its structure.

19 Claims, 4 Drawing Sheets

METHOD FOR MICROENCAPSULATION OF AGRICULTURALLY ACTIVE SUBSTANCES

BACKGROUND OF THE INVENTION

1. Field of Invention

The present invention relates to a method for microencapsulating agriculturally active substances and, more specifically, to the production of microencapsulated chemical and/or biological actives having improved resistance to environmental degradation, especially that caused by exposure to ultra-violet (UV) light. Said actives can be any UV sensitive synthetic or natural or biologically derived pesticide.

The use of microencapsulation as a means of controlling the release of actives, of improving handling via reduced toxicity and of improving environmental stability has been documented. Without such protection, the effectiveness of such actives can be drastically reduced by numerous factors including volatilization and degradation caused by exposure to ultra-violet light. By use of the process described herein, the resistance of UV sensitive chemical and/or biological actives to such losses can be greatly reduced.

2. Prior Art

A number of microencapsulation systems have been proposed for prodding protection of agriculturally active substances.

One method suggested in U.S. Pat. No. 3,839,561 utilizes diisophorone derivatives to protect active cyclopropane carboxylic acid compounds from ultra-violet induced degradation. Similarly, U.S. Pat. No. 4,094,969 describes the use of a sulfonated copolymer of catechin and leucocyanidin as a UV stabilizer. In both cases, however, the formulations suggested do not maintain the sunscreen and active in close enough contact to be effective.

In U.S. Pat. No. 3,242,051, a method for coating materials by phase separation is described. Gelatin and various carboxylated polymers such as gum acacia and ethyl cellulose are used to form the coating. The use of a similar ethylcellulose/gelatin system is described by Ignoffo and Batzer in "Microencapsulation and Ultraviolet Protectants to Increase Sunlight Stability of an Insect Virus", *J. of Econ. Entomology*, Vol. 64, pp. 850–853 (1966), and the use of a chlorophyll green/gelatin system is described in U.S. Pat. No. 2,090,109. In these cases, however, the materials have less than desirable environmental stability. Another disadvantage of these polymers is that they are not always capable of keeping the sunscreening agent within the capsule wall.

Encapsulation of actives by interfacial polycondensation is described in U.S. Pat. Nos. 4,280,833 and 4,417,916. The actives thus formed have a skin or thin wall of polyurea which improves release characteristics and environmental stability. In the process, lignin sulfonate is used as an emulsifier.

The use of lignin in controlled release of actives is also known in prior art. The preparation of controlled release composites of lignin and biologically active materials is described in U.S. Pat. No. 3,929,453 (Re. 29,238). The composites described are obtained by coprecipitation-inclusion from an aqueous alkaline lignin solution, or by the elimination of a common solvent from a lignin-biologically active organic agent mixture. Preparation of reversibly swellable lignin gels is described in U.S. Pat. Nos. 4,184,866 and 4,244,729. The described gels are formed by crosslinking lignin with epichlorohydrin and are able to sustain the release of water-soluble and water-insoluble pesticides. The use of other crosslinking agents such as formaldehyde and glutaric dialdehyde is described in a related U.S. Pat. No. 4,244,728. The use of said gels for UV protection, however, is not disclosed in any of these patents.

The use of sunscreen agents in combination with encapsulation is described in U.S. Pat. No. 4,844,896. Suggested sunscreen agents include methyl orange, malachite green, methyl green and other colored dyes, and suggested encapsulating agents include Eudragit L, Eudragit S, polyacrylic acid and other polyacrylates. It is claimed that such systems keep the sunscreen agent within the capsule. Incorporation of the sunscreen into the capsule wall is not disclosed, however, and the problem of sunscreen catalyzed degradation is not addressed.

The use of lignin or lignin in combination with polyacrylate materials as an encapsulating agent is described in International Application No. PCT/US92/03727. While lignin is disclosed as a sunscreen in this application, the procedures used to make capsules are complex and require a number of different chemicals.

The objective of this invention, on the other hand, is to incorporate ultra-violet sunscreens, and more specifically sulfonated lignins, sulfonated lignites, naphthalene sulfonates and other related compounds, directly into the wall of the capsule. Chemical bonds keep the sunscreen agents from diffusing out of the capsule where they are ineffective. A further objective of incorporation of the sunscreen into the capsule wall is to minimize sunscreen catalyzed degradation of sensitive actives.

Still another objective of the invention is to minimize the number of ingredients needed in the encapsulation procedure, thereby simplifying the overall process.

Other objectives and advantages of the invention will become evident on reading the following detailed description.

SUMMARY OF THE INVENTION

The ultra-violet absorbing properties of lignosulfonates such as sulfonated lignins derived from the sulfite pulping of wood or by sulfonation of lignins derived from the kraft pulping of wood, sulfonated lignites derived from the sulfonation of lignite coal, sulfonated tannins derived by the sulfonation of bark tannins, synthetically prepared naphthalene sulfonates and other related compounds are well established. The functionality of the phenolic and other aromatic, carbonyl, catecholic and carboxyl groups contribute to the ability of these types of compounds to absorb UV light.

It has also been established that certain modifications such as high temperature and other types of oxidation and/or azo-coupling as described in U.S. Pat. No. 4,846,888 can significantly increase the absorbance of these compounds particularly in the case of lignin sulfonates. It is also well known that compounds of this type can effectively dissipate the energy associated with the absorption of UV light internally thereby preventing transfer to other proximate actives.

Under specific conditions sulfonated lignins and sulfonated tannins react with proteins such as, but not limited to, gelatin to form insoluble compounds. When crosslinked, these complexes have low solubility under acidic or neutral conditions but are soluble in alkaline systems.

Also, under specific conditions proteins and carboxylated compounds such as gum arabic interact to form complexes of limited solubility. This interaction is the basis for microencapsulation of many pharmaceutical materials.

In the present invention, a similar system is used to encapsulate agriculturally active materials. The system employed in the present invention, however, utilizes lignosulfonates (e.g. sulfonated lignin), sulfonated lignite, sulfonated tannins, naphthalene sulfonates and/or other related compounds in combination with a protein such as a high bloom gelatin to form the capsule wall. The capsule wall formed by the interaction of these materials is durable and has an ultra-violet protectant as an integral part of its structure. The present invention also has the advantages of requiring minimum mounts of chemicals to produce, it is easy to use and the components of the cell wall are non-toxic and environmentally safe.

BRIEF DESCRIPTION OF THE DRAWINGS

The drawings illustrate the best mode presently contemplated of carrying out the invention.

In the drawings:

FIG. 1 is a graph of the percent degradation over time of parathion encapsulated with a sulfonated lignin as the UV protectant;

FIG. 2 is a graph of the percent degradation over time of parathion encapsulated with a sulfonated lignite as the UV protectant;

FIG. 3 is a graph of the percent degradation over time of parathion encapsulated with an azo-lignosulfonate as the UV protectant; and FIG. 4 is a graph of the percent degradation over time of parathion encapsulated with a sulfonated lignin as the UV protectant as compared to parathion emulsified with a sulfonated lignin in a non-encapsulated formulation.

DETAILED DESCRIPTION OF THE PREFERRED EMBODIMENT

It has been found that the UV sensitivity of agricultural actives including chemical and biological actives can be greatly reduced by encapsulation according to this invention. Such actives include any UV sensitive synthetic, natural, or biologically derived pesticide. As used herein the term "pesticide" has its normal connotation, and is intended to encompose insecticides, herbicides, fungicides, rodenticides, molluscicides, miticides, ovicides, algicides, larvacides, bactericides, and nematocides. For example, the UV sensitive, agriculturally active agent might be a biologically derived pesticide such as a virus, a bacterium, a nematode or a fungi. Viruses include, but are not limited to, the nuclear polyhedrosis virus (NPV) of the bullworm, *Hellothis zea*, of the gypsy moth *Lymantria dispar*, of the Douglas fir tossock moth, *Orgia pseudotsugata*, of the European pine saw fly *Neodiprion sertifer* or of *Autographa californica* or of *H. virescens*. Bacteria known to be insecticidal agents, include but are not limited to *Bacillus thuringiensis, Bacillus Sphaericus, Bacillus Popilliae* and *Bacillus Cereus* may also be encapsulated. Examples of possible nematodes include *Neoaplectana carpocapsae, Octomyomermis muspratti, Steinemema carpocapsae* and *Romanomermis culiciuora*. Examples of possible fungi include *Verticillium lecanii* and *Entomophthora* genus. Chemical toxins include but are not limited to pyrethrum, a naturally derived insecticide; pyrethroids i.e. synthetic copies of pyrethrum, such as allethrin, cyfluthrin, cypermethrin, fenothrin, flucythrinate or indothrin; and organophosphates, such as crufomate, dursban, dicrotophos, parathion or phorate.

Any lignosulfonate, sulfonated lignite, sulfonated tannin or related compound such as naphthalene sulfonates or condensed naphthalene sulfonates or condensed naphthalene sulfonates can be used as a UV protectant in the invention. These compounds are well known and are derived from the sulfite pulping of wood, by sulfonation of lignins derived from the kraft pulping of wood, by sulfonation of tannins derived from wood barks, etc. The lignin materials used are typically in the salt form (i.e. sodium, potassium, etc.). Preferable materials are those with high molecular weight, strong absorptivities in the 290–400 nm wavelength range and sufficient sulfonation to ensure reaction with the proteins (e.g., gelatin, enzymes, etc.).

The lignosulfonates which may be utilized as the UV protectant materials in the practice of and to obtain the novel protein/UV protectant complex of the present invention are the treated or untreated spent sulfite liquors containing the desired effluent lignosulfonate solids obtained from wood conversion as the sulfite waste pulping liquor. These, as indicated, may be utilized in the "as is" or whole liquor condition. They may also be utilized as a purified lignosulfonate material from, or in which the sugars and other saccharide constituents have been removed and/or destroyed, or additionally inorganic constituents have been partially or fully eliminated. Also sulfonated or sulfoalkylated kraft lignin can be used as an adequate UV protectant material.

As used herein, the term "kraft lignin" has its normal connotation, and refers to the substance which is typically recovered from alkaline pulping black liquors such as are produced in the kraft, soda and other well known alkaline pulping operations. The term "sulfonated lignin", as used in the specification refers to the product which is obtained by the introduction of sulfonic acid groups into the kraft lignin molecule, as may be accomplished by reaction of the kraft lignin with sulfite or bisulfite compounds, so that kraft lignin is rendered soluble in water. As used herein, the term "sulfite lignin" refers to the reaction product of lignin which is inherently obtained during the sulfite pulping of wood, and is a principle constituent of spent sulfite liquor. The term "lignosulfonate" ($LSO_3$) encompasses not only the sulfite lignin, but also the sulfonated lignin herein above described. Any type of lignosulfonate that is hardwood, softwood, crude, or pure may be employed. Preferably, lignosulfonates in their as is or whole liquor condition are employed. For example calcium lignosulfonates, sodium lignosulfonates, ammonium lignosulfonates, modified lignosulfonates and mixtures or blends thereof may all be utilized herein. Lignosulfonates are available from numerous sources in either aqueous solution or dried powder forms. For example Lignotech USA, Inc. sells lignosulfonates under the trade designations Lignosol, Norlig, and Marasperse which are appropriate for use in the present invention.

As noted previously, napthalene sulfonates or condensed naphthalene sulfonates may also be used as the UV protectant. Naphthalene sulfonates are well known, and are typically synthesized via sulfonation of napthalene, and napthalene condensates.

A number of proteins can be used along with the UV protectant to form the capsule wall. Proteins such as an albumin, agar-agar, algen, gluten, casein, fibrin or gelatin may be used as the protein source. The preferred protein is gelatin with high bloom strengths as they give the strongest capsule walls.

In the invention, the UV protectant and gelatin are dissolved in a neutral to weak alkaline solution to prevent reaction. An agriculturally active compound (e.g., an active chemical or biological pesticide such as a, herbicide, insecticide, etc.) is then dispersed in or emulsified into the mixture using standard dispersion/emulsification methods.

The pH of the resulting dispersion or emulsion is slowly lowered to between 6.5 and 8.0 by addition of dilute acid. Acids such as hydrochloric acid (HCl), sulfuric acid ($H_2SO_4$), nitric acid ($HNO_3$), phosphoric acid ($H_3PO_4$) or acetic acid ($CH_3COOH$), may be used to adjust the pH of the emulsion. When the pH reaches the isoelectric point of the gelatin, positively charged groups capable of reacting with negative charge groups on the UV protectant are generated. Coacervation occurs resulting in capsule formation. If pH adjustment is desired, caustic (NaOH) can be used to neutralize the resulting mixture. Formaldehyde can also be added to harden (i.e., crosslink) the capsule wall material. Other potential crosslinking agents in addition to formaldehyde include acetaldehyde, glyceraldehyde, malonic acid dialdehyde and glyoxal.

By varying the ratio of protectant and gelatin, the amount of protectant introduced into the capsule wall can be varied. Capsule wall thickness can be controlled by the addition rate of acid during coacervation. Coacervation can also be effected by adding to the emulsion formed in steps 1 and 2 a salt solution using salts such as $Na_2SO_4$ (sodium sulfate), sodium citrate, sodium tartrate, sodium acetate or NaCl (sodium chloride). Reference is made to U.S. Pat. No. 2,800,458 which describes this technique.

EXAMPLE I

This example illustrates the general procedure for producing an encapsulated agricultural active. One gram of high bloom gelatin was dissolved in 95 grams of 40° C. distilled water. Two grams of sulfonated lignin (Lignosol SFX-65) was added to the gelatin solution and the pH of the resulting mixture was adjusted to pH 6.5 with 0.1N HCl Twenty grams of technical parathion was emulsified into the lignin gelatin solution using a high shear mixer. While maintaining 40° C with stirring, the pH of the parathion emulsion was lowered to pH 5.0 by further addition of 0.1N HCl. The mixture was then poured slowly into 300 grams of water containing 10 grams of 37% formaldehyde chilled in an ice bath. The mixture was allowed to stir for 15 minutes and the pH was adjusted to 6.5 with 0.5N NaOH.

EXAMPLE II

This example illustrates the UV protection imparted by the invention. Samples of parathion encapsulated according the procedure described in Example I were sprayed onto microscope slides. The slides were allowed to dry and suspended equi-distant from the light source in a light box. A lamp which produced a spectrum similar to that of natural sunlight was used in the experiment. After certain time intervals, the slides were removed and the samples were analyzed for remaining parathion content. Control samples containing technical parathion only were run concurrently with the samples. The results obtained indicated that degradation resulting from exposure to simulated sunlight was significantly less in the encapsulated samples with greater than 50% actives still available after four weeks of continuous exposure (See FIG. 1).

EXAMPLE III

This example illustrates the effectiveness of a sulfonated lignite protectant. Technical parathion was encapsulated with a combination of a sulfonated lignite and high bloom gelatin as described in Example I and exposed to simulated sunlight as described in Example II. Analysis of the resulting exposed samples indicated UV protection similar to that obtained with sulfonated lignin (See FIG. 2).

EXAMPLE IV

This example illustrates the superior effectiveness of an azo-lignosulfonate protectant. An azo-lignosulfonate was prepared from Marasperse CBOS-6 a sulfonated lignin product available from Lignotech USA, Inc. and p-aminobenzoic acid using the methods described in U.S. Pat. No. 4,846,888. Technical parathion was encapsulated with a combination of a this azo-lignosulfonate and high bloom gelatin as described in Example I and exposed to simulated sunlight as described in Example II. Analysis of the resulting exposed samples indicated UV protection greater than that obtained with either sulfonated lignin or sulfonated lignite (See FIG. 3).

EXAMPLE V

This example illustrates the superior effectiveness of encapsulation over addition of lignosulfonate only. Technical parathion was encapsulated with a combination of a sulfonated lignin (Marasperse CBA-1) and high bloom gelatin as described in Example I and exposed to simulated sunlight as described in Example II. Analysis of the resulting exposed samples indicated UV protection much greater than that obtained using an emulsified parathion non-encapsulated formulation containing an equal amount of Marasperse CBA-1 (See FIG. 4).

Various modes of carrying out the invention are contemplated as being within the scope of the following claims particularly pointing out and distinctly claiming the subject matter regarded as the invention.

I claim:

1. A method for encapsulating an ultra-violet sensitive agriculturally active pesticide in a protective capsule wall, comprising the steps of:

dissolving a protein and an ultra-violet protectant selected from the group consisting of a lignosulfonate, a sulfonated lignite, a sulfonated tannin, a naphthalene sulfonate, a condensed naphthalene sulfonate and an azolignosulfonate in a solution;

mixing a pesticide in said solution to form an emulsion;

coacervating the emulsion to form capsules having a protein/ultra-violet protectant complex as a capsule wall; and recovering the capsules.

2. The method of claim 1 wherein the pesticide is a pyrethroid.

3. The method of claim 2 wherein the pyrethroid is selected from the group consisting of allethrin, cyfluthrin, cypermethrin, fenothrin, flucythrinate and indothrin.

4. The method of claim 1 wherein the pesticide is an organophosphonate.

5. The method of claim 4 wherein the organophosphonate is selected from the group consisting of crufomate, dursban, dicrotphos, parathion and phorate.

6. The method of claim 1 wherein the pesticide is pyrethrum.

7. The method of claim 1 wherein the pesticide is selected from the group consisting of a virus, a bacterium, a nematode and a fungi.

8. The method of claim 1 wherein said pesticide is a nuclear polyhedrosis virus and is selected from the group consisting of *Heliothis zea, H. virescens, Lymantrai dispar, Orgai pseudotsugata, Neodiprion sertifer,* and *Autographa californica.*

9. The method of claim 1 wherein said pesticide is a bacterium and is selected from the group consisting of *Bacillus thuringiensis, Bacillus sphaericus, Bacillus popilliae,* and *Bacillus cereus.*

10. The method of claim 1 wherein said pesticide is a nematode and is selected from the group consisting of *Neoaplectana carpocapsae, Octomyomermis muspratti, Steinemema carpocapsae* and *Romanomermis culiciuora.*

11. The method of claim 1 wherein said pesticide is a fungi and is selected from the group consisting of *Verticillium lecanii* and *Entomophthora genus.*

12. The method of claim 1 wherein said protein is selected from the group consisting of albumin, agar-agar, algen, gluten, casein, fibrin and gelatin.

13. The method of claim 1 wherein the ultra-violet protectant is modified to have increased ultra-violet absorbance in the 290–400 nm range.

14. A process for preparing encapsulated pesticides comprised of the following steps:

i. dissolving a protein selected from the group consisting of albumin, agar-agar, algen, gluten, casein, fibrin and gelatin, and an ultra-violet protectant selected from the group consisting of a lignosulfonate, a sulfonated lignite, a sulfonated tannin, a naphthalene sulfonate, a condensed naphthalene sulfonate and an azo-lignosulfonate, in a solution having a pH of about 6.0 to 8.5;

ii. emulsifying a pesticide in said solution;

iii. acidifying the resulting emulsion to a pH close to the isoelectric point of the protein by controlled addition of acid to form a coacervated mixture containing a protein/ultra-violet protectant complex as a capsule wall;

iv. transferring the coacervated mixture to a chilled water bath; and isolating said capsules.

15. The process of claim 14 further including the step of hardening the capsule wall prior to isolating said capsules.

16. The process of claim 15 wherein the step of hardening comprises adding a crosslinking agent to said chilled water bath.

17. The process of claim 16 wherein the crosslinking agent is selected from the group consisting of formaldehyde, acetaldehyde, glyceraldehyde, malonic acid dialdehyde and glyoxal.

18. The process of claim 14 wherein the step of isolating said capsules comprises filtration.

19. The process of claim 14 further including the step of neutralizing said coacervated mixture prior to isolating said capsules.

* * * * *

UNITED STATES PATENT AND TRADEMARK OFFICE
CERTIFICATE OF CORRECTION

PATENT NO. : 5,552,149
DATED : September 3, 1996
INVENTOR(S) : Stuart E. Lebo, Jr. et al It is certified that error appears in the above-indentified patent and that said Letters Patent is hereby corrected as shown below:

Col. 8, line 9          After ";" and before "and" insert ---v.---.

Signed and Sealed this

Fourteenth Day of January, 1997

Attest:

BRUCE LEHMAN

*Attesting Officer*          *Commissioner of Patents and Trademarks*